(12) United States Patent
Coupard et al.

(10) Patent No.: US 7,589,244 B2
(45) Date of Patent: Sep. 15, 2009

(54) PROCESS FOR THE PRODUCTION OF PROPYLENE FROM A FEED COMPRISING OLEFINS CONTAINING FOUR AND/OR FIVE CARBON ATOMS WITH CO-PRODUCTION OF DESULPHURIZED GASOLINE WITH A HIGH OCTANE NUMBER

(75) Inventors: Vincent Coupard, Vaulx En Velin (FR); Karine Surla, Saint Cyr sur le Rhone (FR)

(73) Assignee: Institut Francais de Petrole, Rueil Malmaison Cedex (FR)

( * ) Notice: Subject to any disclaimer, the term of this patent is extended or adjusted under 35 U.S.C. 154(b) by 384 days.

(21) Appl. No.: 11/582,564

(22) Filed: Oct. 18, 2006

(65) Prior Publication Data
US 2007/0100182 A1    May 3, 2007

(30) Foreign Application Priority Data
Oct. 19, 2005    (FR)    ................... 05 10727

(51) Int. Cl.
*C07C 1/00* (2006.01)
*C07C 4/06* (2006.01)

(52) U.S. Cl. .................. 585/324; 585/329; 585/638; 585/639; 585/640

(58) Field of Classification Search ............... 585/324, 585/329, 638, 639, 640
See application file for complete search history.

(56) References Cited

U.S. PATENT DOCUMENTS

| 4,392,002 A | 7/1983 | Cosyns et al. |
| 6,049,017 A | 4/2000 | Vora et al. |
| 2005/0222475 A1 | 10/2005 | Duplan et al. |
| 2006/0063957 A1 | 3/2006 | Louret et al. |

FOREIGN PATENT DOCUMENTS

FR    2 875 234 A    3/2006

*Primary Examiner*—Tam M Nguyen
(74) *Attorney, Agent, or Firm*—Millen, White, Zelano & Branigan, P.C.

(57) ABSTRACT

For producing propylene and co-producing desulphurized gasoline with a high octane number from a catalytically cracked gasoline cut, and a steam cracking C4/C5 cut, conduct at least one one-step oligocracking stage, a selective hydrogenation stage for FCC gasoline and a hydrotreatment stage.

13 Claims, 1 Drawing Sheet

Figure 1:
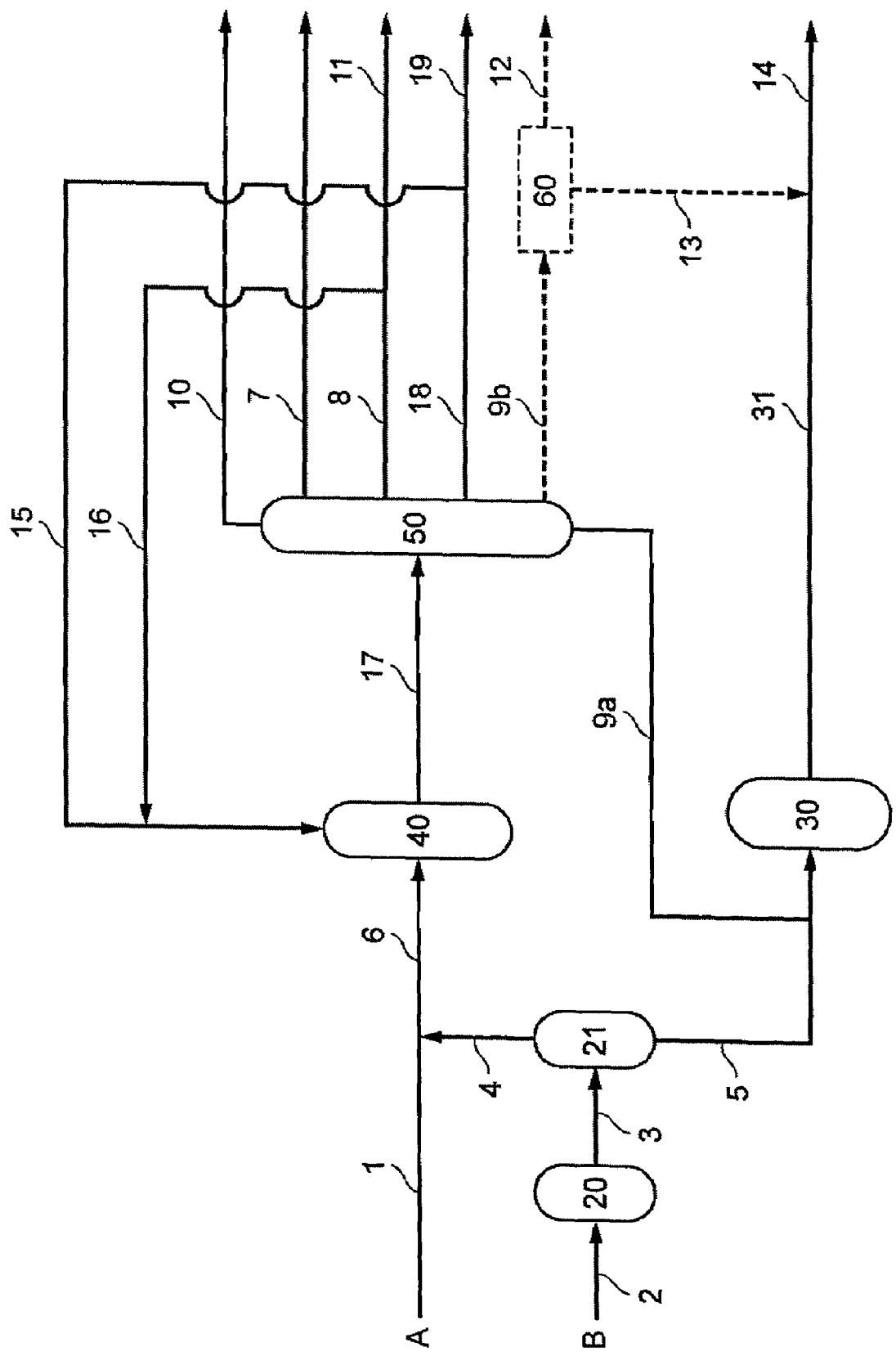

PROCESS FOR THE PRODUCTION OF PROPYLENE FROM A FEED COMPRISING OLEFINS CONTAINING FOUR AND/OR FIVE CARBON ATOMS WITH CO-PRODUCTION OF DESULPHURIZED GASOLINE WITH A HIGH OCTANE NUMBER

FIELD OF THE INVENTION

The invention relates to a process for producing propylene and a desulphurized gasoline with a high octane number from a hydrocarbon feed comprising olefins containing mainly 4 or 5 carbon atoms, said hydrocarbon feed deriving from the C4/C5 cut from a steam cracking unit, and also from the gasoline cut from a fluid catalytic cracking unit (FCC).

Any proportions of each of said two cuts may be used.

The term "steam cracking" designates the unit for steam cracking various hydrocarbon feeds, usually a naphtha cut with a boiling point in the range 100° C. to 350° C., and producing mainly olefins, essentially ethylene and propylene, but also olefins with a higher number of carbon atoms. The C4/C5 olefinic cut from the steam cracking unit is generally produced in a yield which may, depending on the feeds and the operating conditions, be up to 10% by weight and is not directly upgradable.

Thus, it is of advantage to be able to convert it into propylene and gasoline in a process which has been optimized for that purpose; this constitutes the subject matter of the present invention.

The term "FCC" designates the fluidized bed catalytic cracking process for cracking oil fractions with a boiling point of more than about 350° C., generally a vacuum distillate, possibly a deasphalted oil or an atmospheric residue. FCC gasoline corresponds to a cut with a boiling point which is generally in the range 70° C. to 250° C. This gasoline is relatively rich in unsaturated olefinic type compounds, and contains sulphur in amounts which may reach several % by weight.

FCC gasoline requires a specific desulphurization treatment before being incorporated into the gasoline pool, a treatment which uses a selective hydrogenation unit, denoted SHU, and a hydrodesulphurization unit, denoted HDT.

The present invention thus concerns a process for producing propylene and co-producing a desulphurized gasoline with a high octane number, said process combining a one-step oligocracking unit and a desulphurization unit comprising a selective hydrogenation unit (SHU) and a hydrodesulphurization unit (HDT).

The term "one step oligocracking unit" as used in the remainder of the text means a process in which both oligomerization of light olefins, typically C4 to C6, forming heavy olefins, typically C8 to C12, and simultaneous cracking of said heavy olefins into olefins which are mainly lighter than those of the starting feed, principally propylene.

The catalyst used to carry out one-step oligocracking is a dedicated catalyst which is more selective for propylene without cracking any paraffins which may be present in the feed. Further, it is cheaper than two step processes which separate the oligomerization step for the light olefins and the step for cracking the heavy olefins already formed.

In the remainder of the text and using the vocabulary of the skilled person, the terms "C4, C5, Cn cut" designate sets of hydrocarbon molecules mainly containing 4, 5 or n carbon atoms. Clearly, delimitation of said sets, termed cuts, is not strict and in a C5 cut, for example, there is a certain percentage of the adjacent C4, C6 cuts. As a function of the quality of the separation units, usually distillations, said percentage may be limited to less than 5% by weight.

A broad cut characterized by a range, for example C4/C6, means the ensemble of hydrocarbon molecules includes C4 and C6; the remark made above regarding the amount of the adjacent cuts, in this case C3 and C7, is again applicable.

SURVEY OF THE PRIOR ART

The present invention describes a process for producing propylene from an olefinic cut containing mainly C4/C5 and an FCC gasoline, which may be introduced in any proportions.

French patent FR-A-2 608 595 describes a metathesis process which converts an ethylene+n-butene mixture into propylene.

One of the advantages of the process of the invention over that of metathesis is that propylene is produced from olefinic compounds contained in C4/C5 cuts, and does not require a massive consumption of ethylene, which is expensive. Further, if it is applied at a steam cracking site, the process of the invention not only does not use ethylene as a feed, but co-produces ethylene with the propylene. This increases the overall propylene-to-ethylene ratio, matching market trends.

The process described in International patent application WO-A-01/04237 is a further process for producing propylene in one step from light olefins using a catalyst comprising a ZSM-5 zeolite in the fluidized state.

Typical operating conditions for this process are a temperature close to 600° C. and a pressure of 0.1 MPa to 0.2 MPa (1 MPa=10 bars).

Under these conditions, the propylene yield is about 30% and may increase to 50% when unreacted C4 and C5 cuts are recycled.

One disadvantage of this process is that fluidized bed technology is expensive as regards investment and the process is relatively difficult to implement. It also results in substantial loss of catalyst by attrition.

in the one step process family (i.e. without prior oligomerization of the C4/C5 fractions), it is also possible to cite a process a description of which can be found in the article "Production of propylene from low valued olefins" in the review "Hydrocarbon Engineering", May 1999.

It is a fixed bed process the catalyst of which is a ZSM-5 type zeolite used in the presence of steam.

The temperature is close to 500° C. and the pressure is in the range 0.1 MPa to 0.2 MPa.

The stated campaign duration is of the order of 1000 hours. The catalyst is regenerated in situ and its overall service life, i.e. the period during which it is used in the reactor before complete renewal, is about 15 months.

The stated propylene yield is about 40% and could rise to 60% when unreacted C4 and C5 cuts are recycled.

This process could produce a relatively high propylene yield.

However, it requires the use of large quantities of steam.

A process described in International patent application WO-A-99/29805 and in European patents or patent applications EP-A-0 921 181 and EP-A-0 921 179 may also be cited.

It concerns a process using an MFI type zeolitic catalyst having a high Si/Al ratio (180 to 1000) to limit hydrogen transfer reactions responsible for the production of dienes and aromatics.

The temperature is close to 550° C., the pressure is close to 0.1 MPa and the space velocity is in the range 10 h$^{-1}$ to 30 h$^{-1}$. This process may be carried out in fixed, moving or fluidized bed reactors.

The catalyst used comprises a MFI type zeolite with a Si/Al (silicon/aluminum atomic ratio) of 180 or more, preferably a ZSM-5 zeolite with a Si/Al ratio in the range 300 to 1000.

Finally, the process described in European patent application EP-A-0 1 195 424 can be cited.

This is a process using a MFI type zeolitic catalyst having a Si/Al ratio of 180 to 1000 or a MEL type zeolitic catalyst having a Si/Al ratio of 150 to 800, these high s/al ratios being necessary to limit hydrogen transfer reactions responsible for the production of dienes and aromatics.

The temperature is in the range 500° C. to 600° C., the partial pressure of olefins is in the range 0.01 MPa to 0.2 MPa and the space velocity is in the range 5 h$^{-1}$ to 30 h$^{-1}$.

U.S. Pat. No. 6,049,017, which may be considered to be the closest prior art, describes a process for producing propylene from an olefinic cut comprising the following succession of steps: a) separation of mono olefins and diolefins from the starting cut; b) separation of normal and iso-olefins carried out on the stream of mono olefins using an oxidizing agent and an acid catalyst; c) cracking normal olefins using a small pore catalyst.

The process described in the present invention does not employ separation of normal and iso-olefins and further, does not only result in the formation of propylene, but also in the formation of an additional quantity of excellent quality gasoline termed, in the context of the present invention, co-production of high octane number desulphurized gasoline. The term "high octane number gasoline" means a MON octane number of more than 80 and an RON octane number of more than 92.

BRIEF DESCRIPTION OF FIG. 1

FIG. 1 shows the basic flowchart of the process of the invention and facilitates comprehension of the detailed description below.

In FIG. 1, the solid lines represent the obligatory units or streams and the dotted lines represent the optional units or streams.

BRIEF DESCRIPTION OF THE INVENTION

The present invention concerns a process for producing propylene and co-producing a desulphurized gasoline with a high octane number from a feed constituted by a C4/C5 cut from a steam cracking unit (A) and a FCC gasoline (B), said process comprising the following steps:

a step for selective hydrogenation (20) of the FCC gas (B) corresponding to the stream (2), producing an effluent (3) sent to a separation unit (21) which produces two fractions, a light fraction (4) which is sent to a one-step oligocracking unit (40) and a mainly C6+ heavy fraction (5) which is sent to a hydrotreatment unit (30);

a one step oligocracking step (4) which treats a mixture of C4/C5 cut from the steam cracking unit (A) corresponding to the stream (1) and the light fraction (4) from the separation unit (21), the effluent (17) from the oligocracking unit (40) being separated in one or more distillation columns (50) into at least 5 cuts:

1) an overhead cut (10) mainly constituted by ethylene;
2) an overhead cut (7) which constitutes the propylene production of the process;
3) an intermediate cut (8) mainly constituted by C4 molecules, a portion (16) of which is recycled to the inlet to the one-step oligocracking unit (40), and a non-recycled portion (11) of which is upgraded to liquefied petroleum gas;
4) an intermediate cut (18) mainly constituted by C5 and C6 molecules, a portion (15) of which is recycled to the inlet to the one step oligocracking unit (40), the non-recycled portion (19) constituting gasoline directed to the gasoline pool;
5) a bottom cut (9a) constituted by C6+ molecules, which is sent to a hydrotreatment unit (30) mixed with the heavy fraction (5) from the separation unit (21), the effluent (31) from said hydrotreatment unit (30) constituting the co-production of desulphurized gasoline with a high octane number.

In certain cases, it is possible to extract from the distillation unit or units (50) a cut (9b) mainly constituted by C6/C8 molecules which is sent to an aromatics extraction unit (60), the effluent (12) from said aromatics extraction unit (60) being upgraded as a petrochemicals base. A portion (13) of said stream (12) may optionally be mixed with the stream (31) to constitute the high octane number desulphurized gasoline (14).

In a variation of the process of the invention, the ensemble of bottom cuts (9a)+(9b) constituted by molecules containing more than 6 carbon atoms (denoted C6+) is sent to a hydrotreatment unit (30) mixed with the heavy fraction (5) derived from the separation unit (21), effluent (31) from said hydrotreatment unit (30) constituting the co-production of high octane number desulphurized gasoline.

The recycle ratio for the C5/C6 cut (stream 15+16) withdrawn from the one step oligocracking unit (40) is generally in the range 1 to 5, and preferably in the range 2 to 4.

The catalyst used in the one step oligocracking unit (40) comprises at least one zeolite having form selectivity, said zeolite having a Si/Al atomic ratio in the range 50 to 500, preferably in the range 75 to 150.

The catalyst used in the one step oligocracking unit (40) may be a zeolite with form selectivity belonging to a first group constituted by one of the following structures: MEL, MFI, NES, EUO, FER, CHA, MFS, MWW, or it may be constituted by any mixture of the elements of this first group.

The catalyst used in the one step oligocracking unit (40) may also be a zeolite with form selectivity belonging to a second group constituted by the following zeolites: NU-85, NU-86, NU-88 and IM-5, or it may be constituted by any mixture of the elements of this second group.

The one step oligocracking unit (40) generally operates under the following operating conditions:

Temperature in the range 450° C. to 580° C., pressure in the range 0.1 MPa to 0.5 MPa and space velocity in the range 1 h$^{-1}$ to 10 h$^{-1}$ with respect to the fresh feed entering the unit (stream (6)).

The process for producing propylene and co-producing a high octane number desulphurized gasoline of the invention optionally comprises a unit for extracting aromatics (60) treating the mainly aromatic stream (9b) extracted from the distillation separation unit (50). A portion (13) of the effluent from the aromatics extraction unit (60) may be mixed with the effluent (31) from the hydrotreatment unit (30) to constitute the co-production of high octane number desulphurized gasoline (14).

DETAILED DESCRIPTION OF THE INVENTION

The feed for the process of the invention is constituted by two components, a C4/C5 olefinic cut from steam cracking (A), denoted stream (1), and a gasoline cut from catalytic cracking (B), denoted stream (2) and designated the "ex FCC gasoline" in the remainder of the description.

The ex FCC gasoline (B) is sent to a selective hydrogenation unit (20) operating under conventional operating conditions for this type of unit and over a catalyst which is preferably based on a group VIII element deposited on γ alumina. The aim of this selective hydrogenation unit (20) is to eliminate the double bonds characteristic of diolefins.

The external acidic surface of the catalyst must not be too high, to limit polymerization reactions on the catalyst surface. When nickel is used as the metal, its content is in the range 5% to 25% by weight, preferably in the range 7% to 20% by weight. The catalyst is sulphurized to passivate the surface nickel atoms.

The operating conditions for the selective hydrogenation unit are selected so that the effluent remains in the liquid state, i.e. 120° C. to 200° C., under pressures of 0.5 MPa to 40 MPa. The quantity of catalyst used to carry out the selective hydrogenation reaction is typically in the range 2 $m^3$ to 8 $m^3$ of catalyst per $m^3$ of treated fresh feed.

The hydrogen is introduced in an amount of 5% to 30% molar above the stoichiometric quantity, preferably 10% to 20% above the stoichiometric quantity.

The effluent (3) from the selective hydrogenation unit (20) is sent to a distillation unit (21) which can separate the effluent into a light fraction (4) and a heavy fraction (5).

The light fraction (4) constituted by carbonaceous compounds containing less than 6 carbon atoms is mixed with the C4/C5 ex steam cracking cut (1).

The resulting mixture (6) is sent to the one step oligocracking unit (40).

The effluent (17) from the one step oligocracking unit is separated in one or more distillation columns into at least 5 streams:

- an overhead stream (10) constituted by light olefins, mainly ethylene, which is upgraded as a petrochemicals base;
- a stream (7) which is essentially constituted by propylene;
- a stream (8) mainly constituted by saturated C4s, which is partially (11) upgraded as liquefied petroleum gas (LPG) and partially (16) recycled to the inlet to the one step oligocracking unit (40);
- an intermediate stream (18) constituted by a fraction mainly containing 5 or 6 carbon atoms, which is at least partially recycled (stream 15) to the inlet to the one step oligocracking unit (40), the other portion (stream 19) being sent to the gasoline pool;
- and a bottom stream (9a) constituted by hydrocarbons containing more than 9 carbon atoms, which is sent as a mixture with the heavy fraction (5) to the hydrotreatment unit (30), the effluent (31) from which constituting the desulphurized gasoline production;
- a stream (9b) which is rich in aromatics is optionally sent to an aromatics extraction unit (60) producing an effluent (12), which can be upgraded as a petrochemicals base. A portion (13) of said stream (12) can be mixed with the stream (31) to form the high octane number desulphurized gasoline (14).

In a variation of the process of the invention, the ensemble of bottom cuts (9a)+(9b) constituted by C6+ molecules is sent to the hydrotreatment unit (30) mixed with the heavy fraction (5) from the separation unit (21), the effluent (31) from said hydrotreatment unit (30) constituting the co-production of high octane number desulphurized gasoline.

The aromatics extraction unit (60) is a conventional unit which is well known to the skilled person, for example an extraction unit using as the solvent a solution containing dimethylsulphoxide (DMSO); a description of this can be found in the work by Chauvel, Lefebre and Castex ("Procédés de pétrochimie: caractéristiques techniques et économiques—Tome 1—Edition Technip, 1985 [Petrochemical processes: technical and economic features—vol 1—published by Technip]).

The heavy fraction (5) from the separation unit (21) is sent to the hydrotreatment unit (30) mixed with the bottom stream (9a) from the distillation column (50). The effluent (31) from the hydrotreatment unit (30) may be mixed with part of the effluent (13) from the aromatics extraction unit (60) to constitute the high octane desulphurized gasoline (14) co-produced by the process.

The catalyst used in the hydrotreatment unit (30) comprises at least one element from group VIII selected from the group constituted by iron, ruthenium, osmium, cobalt, rhodium, iridium, nickel, palladium and platinum, and at least one group VIB element selected from the group constituted by chromium, molybdenum and tungsten, each of said elements being at least partially in the sulphide form.

The catalyst used in the hydrotreatment unit (30) comprises 0.5% to 15% by weight of group VIII metal, said percentage being expressed in the form of an oxide.

The amount by weight of group VIB metal is generally in the range 1.5% to 60% by weight, preferably in the range 2% to 50% by weight.

The group VIII element is preferably cobalt, and the group VIB element is preferably molybdenum or tungsten.

The catalyst support used in the hydrotreatment unit is normally a porous solid such as magnesia, silica, titanium oxide or alumina used alone or as a mixture, for example.

The operating temperature for the hydrotreatment unit (30) is generally in the range 220° C. to 340° C., at a pressure in the range 1 MPa to 5 MPa (1 MPa=10 bars).

The hourly space velocity is in the range from about 1 $h^{-1}$ to 20 $h^{-1}$. The hourly space velocity is defined as the volume of feed per volume of catalyst per hour.

The ratio of the hydrogen flow rate to the feed flow rate is in the range 100 liters/liter to 600 liters/liter, expressed in normal liters of hydrogen per liter of gasoline.

Typically, the catalyst used in the one step oligocracking unit (40) comprises at least one zeolite having form selectivity, said zeolite having a Si/Al atomic ratio in the range 50 to 500, preferably in the range 75 to 150.

The expression "form selectivity" means that the selectivity of the zeolites used in the present invention is induced by the molecular dimensions of their pore structure.

Form selectivity essentially resides in the fact that certain reagent molecules cannot penetrate into the pores and/or that certain products which are formed cannot leave said pores. Further, the zeolite having form selectivity may belong to a first group constituted by one of the following structure types: MEL, MFI, NES, EUO, FER, CHA, MFS, MWW. It may also be constituted by any mixture of the different elements of said first group.

The zeolite with form selectivity may also belong to a second group constituted by the following zeolites: NU-85, NU-86, NU-88 and IM-5. The zeolite may also be constituted by any mixture of elements of said second group.

One advantage of said zeolites with form selectivity is that it results in better propylene/isobutene selectivity, i.e. a propylene/isobutene ratio which is higher in effluents from said oligocracking unit.

The zeolite or zeolites used in the one step oligocracking unit (40) may be dispersed in a matrix based on silica, zirconia, alumina or silica alumina, the proportion of zeolite(s) generally being in the range 15% to 90% by weight, preferably in the range 30% to 80% by weight.

The Si/Al atomic ratios included in the preferred range of the invention may be obtained on manufacture of the zeolite or by subsequent dealumination.

In particular, the following commercially available ZSM-5 zeolites may be used:

CBV 28014 (Si/Al ratio: 140) and CBV 1502 (Si/Al atomic ratio: 75) from Zeolyst International, Valley Forge, Pa., 19482 USA;

ZSM-5 Pentasil with a Si/Al atomic ratio of 125 from Süd-Chemie (Munich, Germany).

The catalyst used in the one step oligocracking unit (40) is generally employed in a moving bed, preferably in the form of beads generally with a diameter in the range 1 mm to 3 mm.

The catalyst from the one step oligocracking unit (40) may also be used in a fixed bed in which case the reactor or reactors used operate alternately in reaction then in regeneration mode.

The regeneration phase typically comprises a phase for combustion of carbonaceous deposits formed on the catalyst, for example using an air/nitrogen mixture or air depleted in oxygen (for example by recirculating fumes), or simply air.

Regeneration may optionally comprise other phases for treatment and regeneration of the catalyst which will not be described in more detail here as it does not constitute a characteristic aspect of the invention.

The one step oligocracking unit (40) is normally operated at a temperature of about 450° C. to about 580° C., with an hourly space velocity (HSV) generally in the range 1 $h^{-1}$ to 10 $h^{-1}$ with respect to fresh feed (stream 6) entering the unit. The hourly space velocity is defined as the mass of feed with respect to the mass of catalyst per hour.

The operating pressure is generally in the range 0.1 MPa to 0.5 MPa.

The conditions for regeneration of the oligocracking catalyst generally employ a temperature in the range 400° C. to 650° C., the pressure usually being close to the pressure used for the oligocracking reaction.

The recycle rate for the C4/C6 cut (sum of streams 15 and 16) from the one step oligocracking unit (40) with respect to the feed flow rate (6) entering said unit varies from 1 to 5, preferably 2 to 4.

Generally, the yield per pass of propylene (stream 7) with respect to the quantity of olefins contained in the fresh feed (stream 6) of the process is more than 19%, preferably more than 22% by weight.

EXAMPLE OF THE INVENTION

The example below provides a simplified material balance of the process of the invention as illustrated in FIG. 1.

The C4/C5 ex steam cracking cut (A) had the following composition:

| Components | Flow rate, kg/h |
|---|---|
| nC4 = | 9672 |
| iC4 = | 4413 |
| Dienes | 22 |
| C4 paraffins | 5893 |
| n + i C5 = | 6500 |
| Cyclo C5 | 2500 |
| C5 paraffins | 1000 |

The ex FCC gasoline cut (B) had the following composition:

| | Stream B |
|---|---|
| Flow rate, kg/h | 29227 |
| Density (d15) | 0.735 |
| Sulphur (ppm by weight) | 380 |
| RHS (ppm by weight) | — |
| MAV* | 3.9 |
| Bromine number | 90 |
| Olefins content (% by volume) | 45 |
| RON | 93.2 |
| MON | 80.5 |
| ASTM D86 5% point | 52° C. |
| ASTM D86 50% point | 92° C. |
| ASTM D86 95% point | 154° C. |

*MAV (maleic anhydride value) is expressed in milligrams (mg) of maleic anhydride reacting with the diolefins (conjugated dienes) contained in one gram of gasoline using the IFP N°9407 standard method.

The one step oligocracking unit (40) functioned with a ZSM-5 type zeolitic catalyst with an Si/Al atomic ratio of 140, said zeolite being dispersed in an $Al_2O_3$ matrix. The proportion of zeolite was 50% by weight. The one step oligocracking unit (40) functioned under the following operating conditions:

Temperature=510° C.

Pressure=0.02 MPa

HSV=(flow rate of fresh feed)/(mass of catalyst)=6.7 $h^{-1}$

The recycle flow rate for the C4/C6 cut, i.e. the sum of streams (15 and 16) from the one step oligocracking unit (40) with respect to the entering feed flow rate (6), was 2.8.

The hydrotreatment unit (30) functioned with a sulphurized NiMo catalyst on alumina of the HR806 type sold by AXENS using the following operating conditions:

Temperature: 290° C.

Pressure: 2 MPa

HSV=4 $h^{-1}$ $H_2$/HC=360 liters/liter.

The selective hydrogenation unit (20) operated with an HR845 catalyst (sold by AXENS) using the following operating conditions:

Temperature: 143° C.

Pressure: 3.2 MPa

HSV: 6 $h^{-1}$ $H_2$/HC: 5 liters/liter.

The effluent from the selective hydrogenation unit (20) was sent to a distillation unit (21) which separated the stream (3) into a light fraction (4) and a heavy fraction (5) the characteristics of which are shown in the following Table 1:

TABLE 1

Performance of selective hydrogenation unit

| | Stream | |
|---|---|---|
| | 4 | 5 |
| Flow rate, kg/h | 10377 | 18850 |
| Yield (%)/stream B | 35.5 | 64.5 |
| Density (d15) | 0.664 | 0.774 |
| Sulphur (ppm by weight) | 48 | 641 |
| RHS (ppm by weight) | 0 | |
| MAV | 0 | 3 |
| Bromine number | 115 | 91 |
| RON | 96.3 | 91.5 |
| MON | 81.9 | |
| ASTM D86 5% point | 29 | 100 |
| ASTM D86 50% point | 44 | 119 |
| ASTM D86 95% point | 64 | 161 |

The aromatics extraction unit (60) is a unit using, as the solvent, a solution containing dimethylsulphoxide (DMSO). A description can be found in the work by Chauvel, Lefebre and Castex "Procédés de pétrochimie: caractéristiques techniques et économiques—Tome 1—Edition Technip, 1985 [Petrochemical processes: technical and economic features—vol 1—published by Technip].

The details of the various streams of FIG. 1 are given in Table 2 below.

Table 3 shows the material balance of the various streams of FIG. 1, with respect to the ensemble of the entering feeds (A+B), i.e. streams (1+2). The propylene yield (stream 7) with respect to the ensemble of entering feeds (A+B), i.e. streams (1+2), was 22.1%.

The yield of desulphurized gasoline (stream 14) with a high MON with respect to the entering feeds (A+B) (stream (1+2) was 35.4%.

The MON of the gasoline produced (stream 14) was 80.5. The RON was 92.7.

The sulphur content in the gasoline produced (stream 14) was less than 50 ppm.

TABLE 2

Mass flow rates (kg/h) of streams in FIG. 1

| | Stream | | | | | |
|---|---|---|---|---|---|---|
| | 10 | 7 | 11 | 19 | 12 | 14 |
| C1 + c2 | 212 | | | | | |
| C2= | 2888 | | | | | |
| C3 | | 957 | | | | |
| C3= | | 13099 | | | | |
| nC4= | | | 1312 | | | |
| iC4= | | | 842 | | | |
| C4 dienes | | | 22 | | | |
| C4 paraffins | | | 7845 | | | |
| n + i C5= | | | | 606 | | |
| Cyclo C5 | | | | 15 | | |
| C5 paraffins | | | | 5126 | | |
| C6= | | | | 107 | | |
| C6 | | | | 934 | | |
| Desulphurized high MON gasoline | | | | | | 20953 |
| Petro bases (BTX) | | | | | 4234 | |

TABLE 3

Overall yields with respect to sum of feeds A + B

| Stream | | Yield/(stream 1 + 2) |
|---|---|---|
| 10 | C1 + c2 | 5.2 |
| | C2 = | 4.9 |
| 7 | C3 = | 22.1 |
| 11 | C4 | 16.9 |
| 19 | C5C6 | 11.5 |
| 12 | BTX | 7.1 |
| 14 | High MON gasoline | 35.4 |

The characteristics of the high octane number desulphurized gasoline (stream 14 are given in Table 4 below:

TABLE 4

Characteristics of high octane number desulphurized gasoline.

| Stream | 14 |
|---|---|
| Flow rate (kg/h) | 20953 |
| Density (d15) | 0.733 |
| Sulphur (ppm by weight) | <50 |
| RHS (ppm by weight) | — |
| MAV | <0.5 |
| Bromine number (g * 100 g) | 78 |
| Olefins content (% vol) | 40 |
| RON | 92.7 |
| MON | 80.5 |

The invention claimed is:

1. A process for producing propylene and co-producing a desulphurized gasoline with a high octane number from a feed constituted by a C4/C5 cut from a steam cracking unit (A) and a FCC gasoline (B), said process comprising the following steps:

a step for selective hydrogenation (20) of the FCC gasoline (B) (stream 2), producing an effluent (3) sent to a separation (21) which produces a light fraction (4) which is sent to a one-step oligocracking unit (40) and a mainly C6+ heavy fraction (5) which is sent to a hydrotreatment unit (30);

in said one step oligocracking unit (40) treating a mixture of C4/C5 cut from the steam cracking unit (A) (stream 1), and the light fraction (4) from the separation unit (21), an effluent (17) from the oligocracking unit (40) being separated in one or more distillation columns (50) into at least 5 cuts:

1) an overhead cut (10) mainly constituted by ethylene;
2) an overhead cut (7) which constitutes the propylene production of the process;
3) a first intermediate cut (8) mainly constituted by C4 molecules, a portion (16) of which is recycled to the inlet to the one-step oligocracking unit (40), and a non-recycled portion (11) of which is upgraded to liquefied petroleum gas;
4) a second intermediate cut (18) mainly constituted by C5 and C6 molecules, a portion (15) of which is recycled to the inlet of the one step oligocracking unit (40), and a non-recycled portion (19) constituting a gasoline directed to the gasoline pool;
5) a bottom cut (9a) constituted by C9+ molecules which is sent to a hydrotreatment unit (30) mixed with the heavy fraction (5) from the separation unit (21), an effluent (31) from said hydrotreatment unit (30) constituting co-production of desulphurized gasoline with a high octane number.

2. A process for producing propylene and co-producing a high octane number desulphurized gasoline according to claim 1, in which a cut (9b) mainly constituted by C6/C8 molecules is extracted from the distillation column or columns (50) which is sent to an aromatics extraction unit (60), a portion (12) of effluent from said aromatics extraction unit (60) being upgraded as a petrochemicals base, and another portion (13) being sent as a mixture with effluent (31) from the hydrotreatment unit (30) to constitute high octane number desulphurized gasoline (14).

3. A process for producing propylene and co-producing a high octane number desulphurized gasoline according to claim 1, in which the catalyst used in the one step oligocracking unit (40) comprises at least one zeolite having form selectivity, said zeolite having a Si/Al atomic ratio in the range 50 to 500, preferably in the range 75 to 150.

4. A process for producing propylene and co-producing a high octane number desulphurized gasoline according to claim 1, in which the catalyst used in the one step oligocracking unit (40) is a zeolite with form selectivity belonging to a first group constituted by one of the following structure types: MEL, MFI, NES, EUO, FER, CHA, MFS, MWW, or constituted by any mixture of the elements of said first group.

5. A process for producing propylene and co-producing a high octane number desulphurized gasoline according to claim 1, in which the catalyst used in the one step oligocracking unit (40) is a zeolite with form selectivity belonging to a second group constituted by the following zeolites: NU-85, NU-86, NU-88 and IM-5 or is constituted by any mixture of the elements of said second group.

6. A process for producing propylene and co-producing a high octane number desulphurized gasoline according to claim 1, in which the one step oligocracking unit (40) operates under the following operating conditions: a temperature in the range 450° C. to 580° C., a pressure in the range 0.1 MPa to 0.5 MPa, and an hourly space velocity in the range 1 $h^{-1}$ to 10 $h^{-1}$ with respect to fresh feed entering the oligocracking unit (stream 6).

7. A process for producing propylene and co-producing a high octane number desulphurized gasoline according to claim 1, in which the catalyst used in the one step oligocracking unit (40) is used in a moving bed, preferably in the form of beads with a diameter in the range 1 mm to 3 mm.

8. A process according to claim 7, wherein the catalyst in said moving bed is in the form of beads having a diameter in the range of 1 mm to 3 mm.

9. A process for producing propylene and coproducing a high octane number desulfurized gasoline according to claim 1, wherein said one step oligocracking cracking unit (40) is conducted with a ratio of the sum of recycle streams (50) and (60) to fresh feed (6) in the range of 1 to 5.

10. A process according to claim 9, wherein the recycle ratio is in the range of 2 to 5.

11. A process for producing propylene and coproducing a high octane number desulfurized gasoline according to claim 8, wherein said one step oligocracking cracking unit (40) is conducted with a ratio of the sum of recycle streams (50) and (60) to fresh feed (6) in the range of 1 to 5.

12. A process for producing propylene and coproducing a high octane number desulfurized gasoline according to claim 6, wherein said one step oligocracking cracking unit (40) is conducted with a ratio of the sum of recycle streams (50) and (60) to fresh feed (6) in the range of 1 to 5.

13. A process for producing propylene and coproducing a high octane number desulfurized gasoline according to claim 7, wherein said one step oligocracking cracking unit (40) is conducted with a ratio of the sum of recycle streams (50) and (60) to fresh feed (6) in the range of 1 to 5.

* * * * *